United States Patent [19]

Ishikawa

[11] Patent Number: 5,385,150
[45] Date of Patent: Jan. 31, 1995

[54] ACUPUNCTURE DEVICE

[76] Inventor: Keihachi Ishikawa, P.O. Box 4611, Stn. E, Ottawa, Canada, K1S 5H8

[21] Appl. No.: 142,964

[22] Filed: Oct. 29, 1993

Related U.S. Application Data

[63] Continuation of Ser. No. 768,601, Oct. 1, 1991, abandoned.

[51] Int. Cl.⁶ .............................................. A61H 39/02
[52] U.S. Cl. ...................................... 128/735; 128/907; 607/150
[58] Field of Search .................... 128/734, 735, 907; 607/145, 150

[56]  References Cited

U.S. PATENT DOCUMENTS

| | | | |
|---|---|---|---|
| 3,207,151 | 9/1965 | Takagi | 128/735 |
| 3,894,532 | 7/1975 | Morey | 128/735 |
| 3,901,214 | 8/1975 | Taaffe | 128/734 |
| 4,052,978 | 10/1977 | Eugenio | 128/735 |
| 4,408,617 | 10/1983 | Auguste | 128/735 |
| 4,848,357 | 7/1989 | Wong et al. | 128/735 |

FOREIGN PATENT DOCUMENTS 850081  7/1981  U.S.S.R. .............................. 128/735

*Primary Examiner*—Stephen C. Pellegrino
*Assistant Examiner*—Guy V. Tucker
*Attorney, Agent, or Firm*—Adrian Zahl

[57]  ABSTRACT

An apparatus is provided for determining acupuncture cutinous points within an animal body, in particular a human body. The apparatus may also provide therapeutic acupuncture treatment in the form of electrical pulses. The apparatus comprises a housing, electrically conductive terminals external to the housing connected to a circuit within the housing adapted to discharge discrete pulse current through one of the terminals.

6 Claims, 2 Drawing Sheets

ACUPUNCTURE DEVICE

The present application is a continuation of application Ser. No. 07/768,601, filed by the applicant on Oct. 1, 1991, now abandoned, based on PCT application no. PCT/CA90/00110, filed Apr. 4 1990.

FIELD OF THE INVENTION

This invention relates to apparatus to determine acupuncture cutinous points on an animal body, in particular a human body. The apparatus may also provide electrical acupuncture treatment to an animal body.

BACKGROUND OF THE INVENTION

Acupuncture is becoming increasingly recognized in the western world for the treatment of certain medical problems and conditions. The traditional meaning of the word "acupuncture" refers to the introduction of needles into body tissue at certain precise points. These points will be referred to herein as "cutinous points." It has been discovered that the traditional needles may be replaced by electrical stimulation to the cutinous points.

In acupuncture work it is particularly important to determine the precise locations of the cutinous points on a patient's body. Apparatuses intended to serve this purpose exist, but these have been relatively large and cumbersome.

It is desirable to provide by way of such a device a simple and compact hand-held unit, that can both locate the cutinous points and provide electrical treatment. The device should ideally be completely enclosed within a case, with one or both of the electrical terminals being integrated into the case. The locate and treatment functions may be provided by the use of a device that operates on a pulse current, wherein the pulsation of the current both provides treatment and operates a signal device that signals when the device is positioned over a cutinous point. The locate function of such a device can take advantage of the fact that the resistivity of the skin at a cutinous point drops substantially. The use of pulse current is particulary adapted to a device that operates with discrete on/off pulses, rather than voltage-modulated pulses, as is found in prior art devices.

OBJECTS OF THE INVENTION

It is an object of the present invention to provide a simple, compact apparatus for determining cutinous points and for providing electrical treatment in the form of a pulse current.

BRIEF DESCRIPTION OF THE INVENTION

According to the present invention there is provided an apparatus for determining cutinous points in an animal body. In a preferred embodiment, the device is adapted to also provide electrical treatment in the form of pulse current to the body. The device is comprised of a housing, first and second electrically conductive terminals external to the housing adapted to make contact with a patient's skin, an electrical circuit within the housing connected to said terminals by way of extension leads, and an electric current source, such as a battery, connected to the circuit. The circuit is adapted to discharge current in discrete pulses through the first terminal.

In a preferred embodiment, the device has a hand-holdable housing and the electrical circuit of the device comprises:

a) a resistor connected to the first terminal;

b) a transistor having first, second and third electrodes, the transistor being adapted to generate a discrete pulse current by the on/off switching thereof, and the first electrode being a base electrode connected to the first terminal through the resistor;

c) a transformer having a primary winding having first and second ends and an intermediary tapping point, the first end of the primary winding being connected to the second electrode and the second end of said primary winding being connected to the second terminal, and the intermediary tapping point being connected to the third electrode through the electrical source;

d) a capacitor connected between said first electrode and said second terminal, the discharge rate of the capacitor being controlled by the resistivity of the skin.

DETAILED DESCRIPTION OF THE PREFERRED EMBODIMENTS

Figure 1:
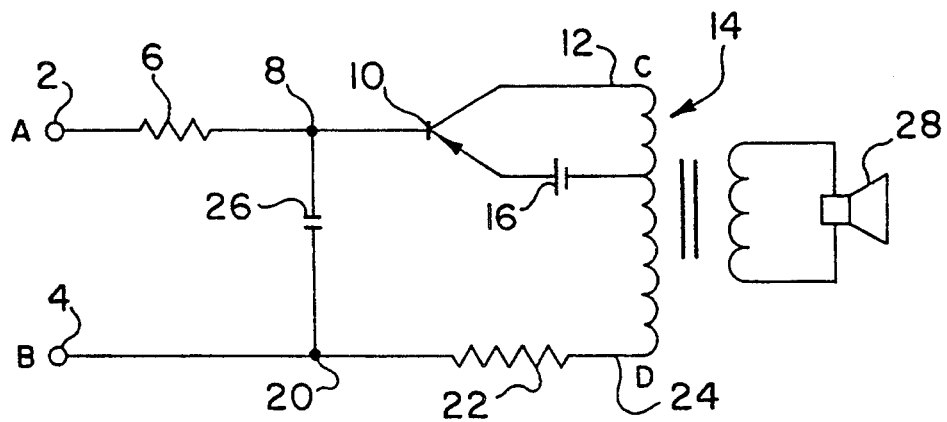
FIG. 1 is a diagrammatic representation of a circuit for use in apparatus according to a first embodiment of the present invention.

Referring to FIG. 1, the circuit of the device has two terminals 2, 4 for making contact with the skin of a human being. The first terminal 2 is connected through a first resistor 6 and through an intermediary point 8 to the base electrode of a transistor 10, another electrode of said transistor being connected to one end 12 of the primary winding of a transformer 14, and a third electrode being connected to an intermediary tapping point 18 of the transformer 14.

The second terminal 4 is connected through an intermediary point 20 and a second resistor 22 to the opposite end 24 of the primary winding.

A capacitor 26 is connected between the intermediary points 8 and 20. The rate of discharge of the capacitor is a function of the resistance between the terminals 2 and 4, with a decreased resistance resulting in a faster rate of discharge, when the capacitor has discharged by a fixed amount, the transistor 10 shuts the current flow off, allowing the capacitor to recharge. Accordingly, as the discharge rate increases as a result of decreased resistance between the terminals when a cutinous point is contacted, the rate of charge/discharge cycles of the capacitor increases, resulting in a faster oscillation of the circuit and a more rapid current pulse rate being discharged from the terminals.

Figure 2:
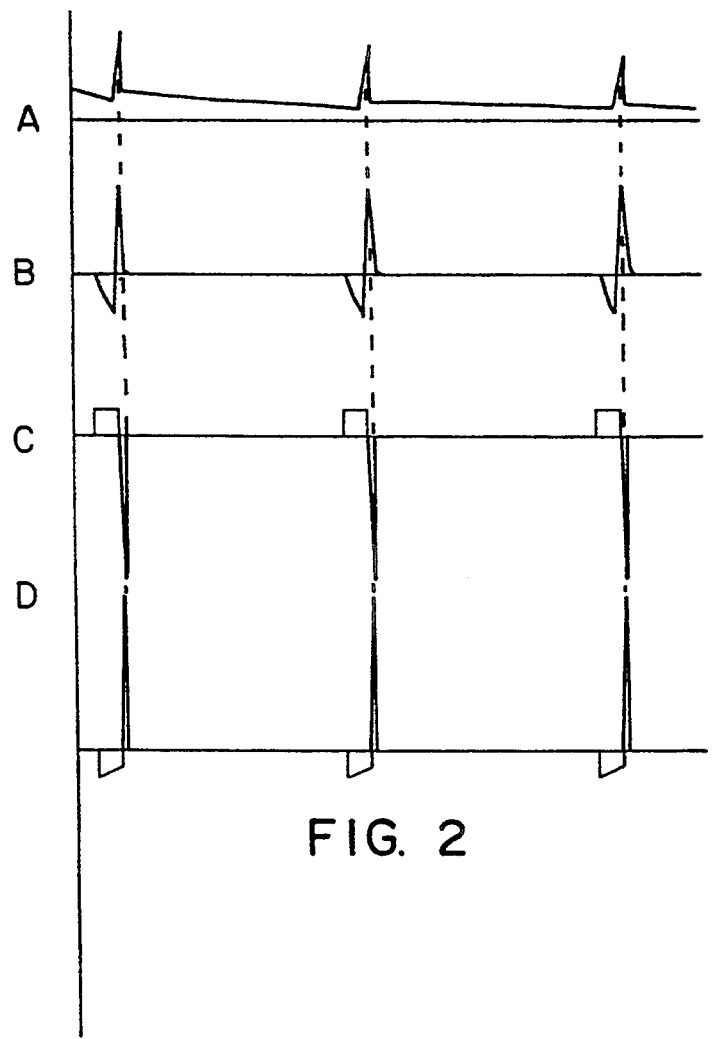
FIG. 2 is graphical representation of the voltage waveform at certain points in the circuit of FIG. 1.

A loudspeaker 28 is connected across a secondary winding of the transformer 14. The waveforms in FIG. 2 are illustrated for the purpose of understanding the operation of the circuit of FIG. 1 as described below.

Figure 3:
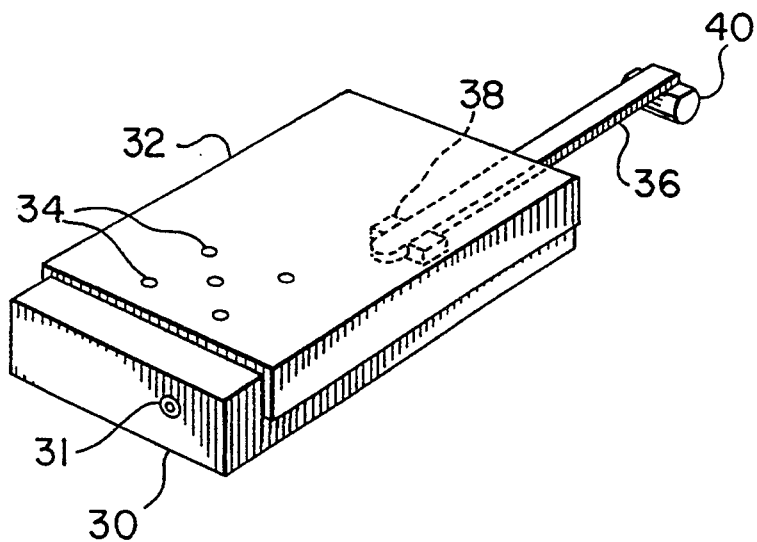
FIG. 3 is a perspective view of apparatus constructed according FIG. 1.
Figure 4:
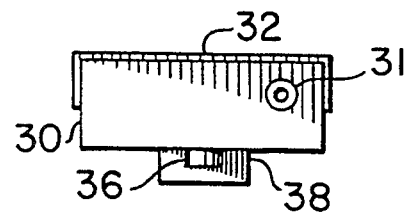
FIG. 4 is a side elevational view of the apparatus of FIG. 1.

The perspective view of the embodiment illustrated in FIG. 3 shows a unit capable of being held in the hand of the doctor or the patient for determining the relevant cutinous points of the patient's body. If the device is held by the doctor, the free hand of the doctor or some other part of his body should make contact with the skin of the patient to complete an electrical circuit. Alternatively, a cord may be plugged into socket 31, as shown in FIGS. 3 and 4. A metallic probe is connected to the free end of the cord and held by the patient.

The device has a rectangular case 30 of plastic or other insulating material. A metallic U-shaped plate 32 is affixed over part of the body and is connected to the terminal 2 in the circuit of FIG. 1. An array of holes 34 extend through the top surface of the case 30 for the transmission of sound from the loudspeaker 28, shown in FIG. 1.

A metallic extendible arm 36 projects beyond the case 30 and is moveable longitudinally. Lateral movement of the arm 36 is restricted by guide members 38, shown in FIGS. 3 and 4. A contact terminal member 40, having a semi-circular cross section, is integrally and electrically attached to the end of arm 36, the arm 36 having an electrical connection to the terminal 4 in the circuit of FIG. 1.

The operation of the device will now be described with reference to FIGS. 1–4. It will be observed that FIG. 2 is a representation of the voltage waveforms at points A, B, C and D of FIG. 1. It will be seen that the voltage oscillates in pulses, with the current at any given moment being either off or operating at generally maximal voltage. In use, terminals 2 and 4 are applied to the skin of a patient and capacitor 26 is charged up. Current then ceases to flow until terminal 4 contacts a cutinous point of the patient. Such cutinous points are substantially more conductive than other parts of the skin—with a typical resistivity of about 50–100 kilohms, as against a normal skin conductivity of between 10 and 20 megohms.

Due to the change in resistivity, capacitor 26 begins to discharge and when its voltage is lower than the supply voltage across terminals 8 and 20 by 0.6 to 0.7 volts, base current of the transistor 10 starts to flow. This completes the circuit through part of the primary winding of transformer 14 back to the negative terminal of battery 16. However, the base current of transistor 10 charges the capacitor 26 back above its threshold and in effect turns the transistor off, causing the collector current to decrease to zero, whereby the transformer 14 generates a negative pulse at point C, as shown in FIG. 2. The winding of transformer 14 is such that an inverted signal is induced at point D. As a result, a positive pulse is produced, which charges capacitor 26 through resistor 22 to an even higher voltage. This ensures that the off state of transistor 10 is maintained. However, the passage of electricity through the patient's skin allows the capacitor 26 to discharge and as soon as the voltage is below the threshold level, the whole sequence is repeated. As the resistance across the patient's skin decreases when a cutinous point is contacted, the capacitor discharges more rapidly, resulting in a faster oscillation of the circuit. The oscillation generates an audible signal through the secondary winding of transformer 14 and miniature loudspeaker 28. The audible signal produced depends on the conductivity of the various locations at which terminals 2 and 4 are located, terminal 2 normally being electrically connected to a metallic portion held in the hand of the patient whilst terminal 4 is connected to a metallic portion which is moved over the skin to determine a cutinous point. In the apparatus of FIG. 3, terminal 4 is connected to the contact member 40.

It is important to observe that point B is negative in relation to point A, and a negative potential is applied in order to stimulate the cutinous points. When a cutinous point is detected and it is desired to stimulate that point, the metallic part corresponding to point B should be maintained in contact with the patient's skin at the respective cutinous point for a short period of time, normally 10–15 seconds. This appears to have substantial advantage over the method of using mechanical stimulation by means of a needle or heat, or other traditional acupuncture technique. It will be understood that a reverse polarity stimulation will not take place although detection of the cutinous point on the patient's skin is still possible.

Figure 5:
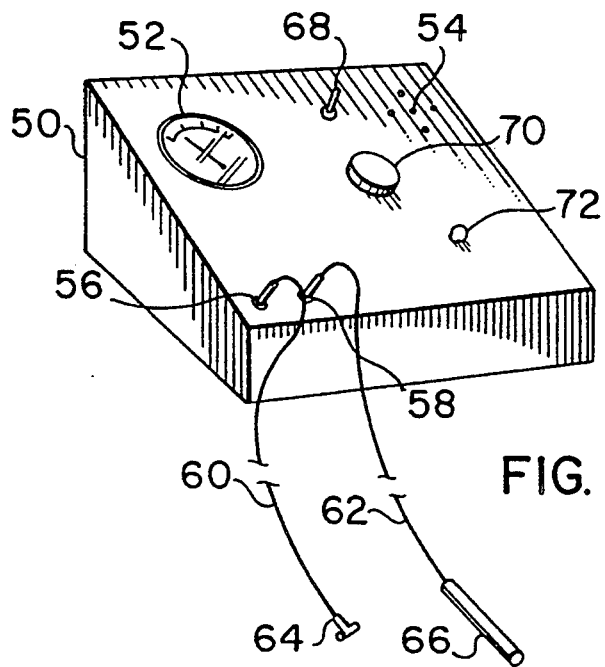
FIG. 5 is a perspective view of a second embodiment of the invention.

Referring to FIG. 5, there is illustrated a further embodiment of the invention which comprises a housing 50 having a sloping upper surface on which is located an indicating meter 52, holes 54 therein for the emergence of sound from loudspeaker 28 of FIG. 1, and plug-in terminals 56 and 58. At the end of the wires are metallic probes 64 and 66, as shown in FIG. 5. The probes 64 and 66 may be placed at any two separate locations on the patient's skin to determine the cutinous points.

The embodiment shown in FIG. 5 is more convenient for use in a doctor's office, while the first embodiment of FIG. 3 is convenient for use either in a doctor's office or at home.

The embodiment of FIG. 5 is also provided with an on-off switch 68, an adjustable current limiter 70 and a volume control 72.

It will be understood that the loudspeaker 28 may be replaced with some other indicating means, such as a lamp or meter.

Other changes and adaptations include the substitution of a higher voltage battery for battery 16, which would allow the omission of resistor 22 and an increase in value of resistor 6. Thus, terminal 4 and transformer end 24 would be directly connected together instead of being indirectly connected through resistor 22. A lower current of 30 to 40 micro-amps could be achieved with this arrangement.

In FIG. 3, the end of arm 36 and/or at least one end of contact terminal member 40 could be tapered to a point to facilitate use around parts of a patient's body, for example the ears. Arm 36 could, if desired, be made non-extendible but fixed in position.

It will be apparent to one skilled in the art that variations and modifications may be made to the embodiments of the invention described above, without departing from the spirit and scope of the invention, as defined in the appended claims.

I claim:

1. An apparatus for determining cutinous points within an animal body, comprising a housing, first and second electrically conductive terminals external to said housing adapted to make contact with the skin of said animal body, an electrical circuit within said housing connected to said terminals by way of extension leads, and an electrical current source connected to said circuit, said electrical circuit adapted to discharge current in discrete pulses through said first terminal and comprising:

a) resistor connected to said first terminal;

b) a transistor having first, second and third electrodes, said transistor being adapted to generate a discrete pulse current by the on/off switching thereof, said first electrode connected to said first terminal through said resistor;

c) a transformer having a primary winding having first and second ends and an intermediary tapping point, the first end of said primary winding being connected to said second electrode and the second end of said primary winding being connected to said second terminal, said intermediary tapping point being connected to said third electrode through said electrical source;

d) a capacitor connected between said first electrode and said second terminal, said capacitor adapted to discharge at an increased rate as the electrical resistivity of the skin drops, thereby generating an increased pulse rate in said pulse current; and e) an indicator means to indicate said pulse current.

2. An apparatus according to claim 1, said indicator means comprising an apparatus for emitting audible pulses at the frequency of said pulse current.

3. An apparatus as claimed in claim 1 wherein said housing is adapted to be held with one hand during use and at least one of said terminals is integral with said housing.

4. An apparatus as claimed in claim 3 wherein both of said terminals are integral with said housing.

5. An apparatus as claimed in claim 3 wherein said first terminal is a positive terminal and said second terminal is a negative terminal and is positioned on an extendible arm engaged to the housing.

6. An apparatus as claimed in claim 5 wherein said extendible arm is adjustable in length.

* * * * *